(12) United States Patent
Baker

(10) Patent No.: US 9,554,574 B2
(45) Date of Patent: *Jan. 31, 2017

(54) GRANULAR TURF SAFE MESOTRIONE COMPOSITIONS

(71) Applicant: OMS INVESTMENTS, INC., Los Angeles, CA (US)

(72) Inventor: Robert D. Baker, Westerville, OH (US)

(73) Assignee: OMS Investments, Inc., Los Angeles, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 14/485,106

(22) Filed: Sep. 12, 2014

(65) Prior Publication Data

US 2015/0005173 A1   Jan. 1, 2015

Related U.S. Application Data

(60) Continuation of application No. 13/656,008, filed on Oct. 19, 2012, now Pat. No. 8,858,973, which is a continuation of application No. 13/279,467, filed on Oct. 24, 2011, now Pat. No. 8,293,259, which is a division of application No. 11/487,774, filed on Jul. 17, 2006, now Pat. No. 8,114,426.

(60) Provisional application No. 60/700,637, filed on Jul. 19, 2005.

(51) Int. Cl.
| | | |
|---|---|---|
| *A01N 25/26* | (2006.01) | |
| *A01N 41/10* | (2006.01) | |
| *C05G 3/02* | (2006.01) | |
| *C05G 3/00* | (2006.01) | |

(52) U.S. Cl.
CPC .............. *A01N 41/10* (2013.01); *A01N 25/26* (2013.01); *C05G 3/0017* (2013.01); *C05G 3/02* (2013.01)

(58) Field of Classification Search
None
See application file for complete search history.

(56) References Cited

U.S. PATENT DOCUMENTS

| 4,082,538 | A  | * | 4/1978  | McRae   | C07C 205/06 |
|---|---|---|---|---|---|
|           |    |   |         |         | 504/118 |
| 5,006,158 | A  |   | 4/1991  | Carter et al. | |
| 6,180,565 | B1 | * | 1/2001  | Detrick | A01N 25/24 |
|           |    |   |         |         | 504/145 |
| 6,890,889 | B1 |   | 5/2005  | Wichert et al. | |
| 8,114,426 | B2 | * | 2/2012  | Baker   | A01N 25/26 |
|           |    |   |         |         | 424/417 |
| 8,293,259 | B2 | * | 10/2012 | Baker   | A01N 25/26 |
|           |    |   |         |         | 424/417 |
| 8,858,973 | B2 | * | 10/2014 | Baker   | A01N 25/26 |
|           |    |   |         |         | 424/417 |
| 2003/0114309 | A1 |   | 6/2003  | Ruegg | |
| 2005/0096226 | A1 | * | 5/2005  | Stock   | A01N 41/10 |
|           |    |   |         |         | 504/141 |

FOREIGN PATENT DOCUMENTS

WO   WO 2007/101620   9/2007

OTHER PUBLICATIONS

International Search Report and Written Opinion for PCT/US2006/027620, 8 pages, mailed Jan. 18, 2008.
Supplemental Extended European Search Report for PCT/US2006/027620, based on EP 06787516.1, mailed Feb. 13, 2012.

\* cited by examiner

*Primary Examiner* — Alton Pryor
(74) *Attorney, Agent, or Firm* — Ulmer & Berne LLP

(57) ABSTRACT

A composition comprising herbicidal mixtures of mesotrione impregnated into or coated on the surface of a granular substrate material such as a fertilizer granule and/or a solid inert carrier material is provided for use to control weeds in turfgrasses without causing damage to the grass and methods for the use thereof.

20 Claims, No Drawings

GRANULAR TURF SAFE MESOTRIONE COMPOSITIONS

CROSS-REFERENCE TO RELATED APPLICATION

This application is a divisional of U.S. patent application Ser. No. 13/656,008, filed Oct. 19, 2012, which is a continuation of U.S. patent application Ser. No. 13/279,467, filed Oct. 24, 2011, now U.S. Pat. No. 8,293,259, which is a division of U.S. patent application Ser. No. 11/487,774, filed Jul. 17, 2006, now U.S. Pat. No. 8,114,426, which claims priority to U.S. Provisional Patent Application No. 60/700,637, filed Jul. 10, 2005, the disclosures of each of which are herein incorporated in their entirety.

BACKGROUND OF THE INVENTION

1. Field of the Invention

The present invention relates generally to granular compositions containing mesotrione herbicides and to methods for the use thereof. More particularly, the compositions of this invention comprise herbicidal mixtures of mesotrione impregnated into or coated on the surface of a granular substrate material such as a fertilizer granule for use to control weeds in turfgrasses without causing damage to the grass.

2. Description of Related Art

Mesotrione is a triketone compound having the chemical structure of (2-[4-methylsulfonyl-2-nitrobenzoyl]-1,3-cyclohexane dione) employing CAS nomenclature. A liquid product containing 40 weight percent mesotrione is being sold under the trademark Callisto® by Syngenta Crop Protection, Inc. as a systemic pre-emergence and post-emergence herbicide for the selective contact and residual control of broadleaf and grassy weeds in field corn, production seed field corn, field corn grown for silage, yellow popcorn and sweet corn. In the context of the present invention, the term "mesotrione" is intended to refer to the triketone compound itself as well as to all formulations containing such compound.

U.S. Pat. No. 5,006,158 describes a wide variety of compounds including mesotrione which are useful as herbicides and can be applied in a variety of ways at various concentrations. The compounds or salts thereof described in U.S. Pat. No. 5,006,158 are described as being formulated into herbicidal compositions, by admixture, in herbicidally effective amounts, with adjuvants and carriers normally employed for facilitating the dispersion of active ingredients for agricultural applications and acknowledges the fact that the formulation and mode of application of such active ingredients may affect the activity of the materials in a given application.

U.S. Pat. No. 5,006,158 further discloses that the diverse active herbicidal compounds or salts disclosed therein can be formulated as granules of relatively large particle size, as wettable powders, as emulsifiable concentrates, as powdery dusts, as flowables, as solutions or as any of several other known types of formulations, depending upon the desired mode of application. The formulations containing the actives are disclosed to contain as little as about 0.5% to as much as about 95% or more by weight of active ingredient. A herbicidally effective amount of the actives is disclosed as depending upon the nature of the seeds or plants to be controlled and the rate of application varies from about 0.01 to approximately 10 pounds per acre, preferably from about 0.02 to about 4 pounds per acre.

Granular formulations wherein the actives are carried on relatively coarse particles as disclosed in U.S. Pat. No. 5,006,158 are usually applied without dilution to the area in which suppression of vegetation is desired. Typical carriers for such granular formulations as described in U.S. Pat. No. 5,006,158 include sand, fuller's earth, attapulgite clay, bentonite clays, montmorillonite clay, vermiculite, perlite and other organic or inorganic materials which absorb or which may be coated with the toxicant. These granular formulations are normally prepared to contain about 0.1% to about 25% of active ingredients which may include surface-active agents such as heavy aromatic naphthas, kerosene or other petroleum fractions, or vegetable oils; and/or stickers such as dextrins, glue or synthetic resins.

In U.S. Pat. No. 6,890,889, herbicidal formulations comprising mesotrione in combination with an adjuvant system were disclosed to optimize post emergent activity on broad-leaved weeds in corn. The preferred adjuvant system to optimize weed control and minimize crop response was disclosed to be a crop oil concentrate (COC). Other adjuvant systems for use in the formulation may comprise liquid compositions such as methylated seed oil (MSO), urea ammonium nitrate (UAN) and ammonium sulfate (AMS). No granular formulations are disclosed.

In Published U.S. Patent Application US 2005/0096226, herbicidal compositions useful for controlling weeds in growing crops such as maize (corn) comprising triketone products including mesotrione in combination with an organic phosphate, phosphonate or phosphinate adjuvant were disclosed which can be prepared as a pre-mix concentrate for formulation in various forms including granular formulations with typical carriers such as sand, fuller's earth, attapulgite clay, bentonite clays, montmorrilonite clay, vermiculite, perlite and other organic or inorganic materials which absorb or which can be coated with the active compound.

However, it appears that mesotrione applied as a liquid in spray form as described in U.S. Pat. Nos. 5,006,158, 6,890,889 and in Published U.S. Patent Application US 2005/0096226 is not effective for use in controlling weeds in turfgrasses without causing unacceptable injury to the grasses. Specifically, previously known mesotrione containing formulations in spray form have demonstrated unacceptable levels of damage/phytotoxicity to a range of turfgrass varieties. Turfgrass varieties as referred to herein include perennial ryegrass (*Lolium perenne*), fine fescue (*Festuca* spp.), Kentucky bluegrass (*Poa pratensis*), tall fescue (*Festuca arundinacea*), zoysiagrass (*Zoysia* spp.), St. Augustinegrass (*Stenotaphrum secundatum*), centipedegrass (*Eremochloa ophiuroides*), and the like and mixtures thereof. In view of this perceived shortcoming of prior liquid mesotrione containing formulations, mesotrione sprays have not been considered to be capable of being employed broadly for effective herbicidal treatment in turfgrass varieties.

Thus, it would be advantageous to provide granular compositions containing mesotrione as an active herbicidal ingredient which can be used to control weeds in turfgrasses such as perennial ryegrass, fine fescue, Kentucky bluegrass, tall fescue, zoysiagrass, St. Augustinegrass, centipedegrass and the like and mixtures thereof without causing unacceptable phytotoxic levels of damage to these grasses.

SUMMARY OF THE INVENTION

It is a primary object of the present invention to provide granular mesotrione containing formulations for safe and effective herbicidal treatment of turfgrass species whereby weeds growing, for example, in a lawn can be controlled without causing undue phytotoxic effects on the grasses themselves.

Another object of this invention is to provide granular turf safe mesotrione compositions for herbicidal treatment of weeds in turfgrasses.

A further object is to provide methods for effective and efficient control of weeds in a turfgrass without causing significant injury to the turfgrass by applying a granular mesotrione containing composition to the grass.

The foregoing and other objects of this invention are achieved by providing a granular herbicidal composition comprising mesotrione coated on or impregnated into a solid granular substrate material, preferably, a fertilizer material. Alternatively, a suitable inert solid carrier material may be employed with or in substitution for the fertilizer material. The resulting compositions have been found to be highly effective for use in controlling the growth of weeds in turfgrasses without causing significant injury to the turfgrass when applied thereto.

DETAILED DESCRIPTION OF THE INVENTION

Illustrative fertilizers which can be employed for mixture with a herbicidal mesotrione ingredient to produce a granular composition of the present invention include a wide variety of fertilizer granules, particles or pellets (which are referred to collectively herein as fertilizer granules) such as organic and inorganic nitrogen-containing compounds comprising urea, urea-formaldehyde condensation products, amino acids, ammonium salts and nitrates, potassium salts (preferably chlorides, sulfates, nitrates) and phosphoric acid and/or salts of phosphoric acid. Also, it should be noted that the fertilizer granules suitable for inclusion in the present mixtures may also contain micronutrients, such as iron, manganese, magnesium, boron, copper, zinc and the like.

The physical forms of the fertilizers to be employed in combination with mesotrione to produce the compositions of the present invention include granules and extruded particles. Fertilizer granule sizes, preferably, should range from about 1.0 to about 5.0 mm diameter (most preferably, about 1.5-3.0 mm). Extruded particle sizes preferably should range from about 0.6 to about 7.0 mm diameter (most preferably, about 1.0-3.0 mm). Particle length preferably should range from about 0.6 to about 10.0 mm (most preferably, 1.0-5.0 mm).

Preferably, the chemical analysis for the fertilizer component to be included in the present compositions, when present, should range from about 1 to about 40% by weight elemental nitrogen (N) (most preferably, about 15-36% by weight); about 1 to about 30% by weight phosphorous as $P_2O_5$ (most preferably, about 1-27% by weight); and about 1 to about 20% by weight potassium as $K_2O$ (most preferably, about 3-15% by weight). The micronutrient content of the fertilizer ingredient, preferably, should range from about 1 to about 20,000 ppm (parts per million).

Preferably, the quantity of mesotrione to be incorporated in combination with the fertilizer component to prepare the compositions of the present invention should range from about 0.05% to about 1.0% (preferably about 0.1-0.5%) by weight of the total composition.

In an alternative embodiment of the present invention, inert solid carriers may be admixed with the mesotrione component either with or without the fertilizer constituent to produce a composition for use in accordance with the present invention.

Suitable inert solid carrier materials for use herein include any of a variety of organic and/or inorganic materials, which absorb or which may be coated with the mesotrione active ingredient and that have been appropriately ground/fractionated/sized, may be employed herein. Suitable organic materials include corncobs, peanut hulls, processed paper pulp, sawdust and the like whereas suitable inorganic materials include limestone, gypsum, sand, vermiculite, perlite, fuller's earth and clays such as attapulgite clays, bentonite clays, montmorillonite clays.

Preferably, the quantity of mesotrione to be incorporated in combination with an inert carrier material to prepare the compositions of the present invention should range from about 0.025% to about 1.25% (preferably about 0.075-0.4%) by weight of the total composition.

The compositions of the present invention may be produced employing any of a variety of processes. For example, the mesotrione can be applied to a fertilizer/inert granule using one or more of the following techniques: (a) as a spray mixture with solvents and/or surfactants; or (b) adhered to the outer surface of the fertilizer/inert granule with an adhesive/sticking agent; or (c) incorporated into a mixture of dry ingredients and a liquid, and then extruded or molded into discrete particles; or (d) impregnated into a porous granule.

Specifically, the compositions of the present invention may be prepared by mixing mesotrione with a granular fertilizer in effective amounts (for example, in a rotating drum container) and mixing the ingredients for a sufficient period of time until the mesotrione is uniformly coated on and absorbed in the fertilizer granules.

Other optional methods which may be employed for producing compositions of the present invention containing mesotrione and a granular fertilizer include:

Dissolving a mesotrione concentrate in a liquid solvent/surfactant blend, then spraying this mixture on a fertilizer and/or inert carrier material so the solution is uniformly absorbed on the substrate particles; or Using mesotrione in a dry powder state, tacking this onto the surface of a fertilizer and/or inert carrier material using a liquid sticking agent or adhesive to obtain a uniform distribution of the mesotrione over the substrate particles.

The compositions of the invention as described above can be applied at various rates to achieve the desired effect of weed control and turf safety. In general, a minimum rate of about 0.15 to about 0.25 lb mesotrione per acre is required to control weeds in turfgrass under the wide range of conditions that are experienced in growing turf, such as geographical location, temperature, soil moisture, weed species and stage of growth, and other factors. In addition, the variables that affect the precision of application of the compositions (for example, the quality and accuracy of the application equipment) make it very likely that higher rates of mesotrione than intended may be applied by users of the products, especially by non-professional users.

Thus, the benefits of this invention, as described herein are very important to enable application of compositions of granular mesotrione without causing undue harm to the turfgrasses to which the composition is applied. To the contrary, liquid mesotrione treatments would be much more likely to cause injury when applied to desirable turfgrasses for the same reasons noted above relating to variability in application rates; particularly, in view of the fact that liquid mesotrione does not exhibit the turf safe features resulting from the use of the compositions of this invention.

In accordance with the present invention, granular herbicidal compositions for use in controlling weeds in a turfgrass without causing significant injury to the turfgrass are provided comprising mesotrione coated on or impregnated into granular substrate materials wherein the granular substrates are solid fertilizer granules, inert solid carrier materials or mixtures thereof. In a preferred embodiment, the solid fertilizer granules are organic or inorganic nitrogen-containing compounds and the composition is formulated to provide a weight percentage of mesotrione when applied to a turfgrass calculated in accordance with the equation:

$$A=X(Y+Z)$$

wherein A is the weight percentage of mesotrione provided by the composition when applied to a turfgrass; X is the application rate in pounds per acre of mesotrione provided when the composition is applied to treat the turfgrass; Y is the weight percentage of Nitrogen in the composition; and Z is the application rate in pounds per acre of Nitrogen provided when the composition is applied to treat the turfgrass.

In the most preferred embodiments of the present invention, it has been found that the herein provided compositions are formulated and methods are provided for use of the compositions in treating perennial ryegrass at application rates of about 0.15 to about 1.0 lb granular mesotrione/acre; for treating fine fescue at application rates of about 0.25 to about 1.0 lb granular mesotrione/acre; for treating Kentucky bluegrass at an application rate of about 1.0 lb granular mesotrione/acre; for treating tall fescue at application rates of about 0.33 to about 1.0 lb granular mesotrione/acre; for treating zoysiagrass at application rates of about 0.15 to about 0.5 lb granular mesotrione/acre; for treating St. Augustinegrass at application rates of about 0.5 to about 1.0 lb granular mesotrione/acre and for treating centipedegrass at an application rate of about 1.0 lb granular mesotrione/acre.

The following specific examples are presented to further illustrate and explain certain aspects of the present invention. However, the examples are set forth for illustration only, and are not to be construed as limiting on the present invention. In the following examples, all percentages and parts are by weight unless otherwise specified.

EXAMPLE 1

This example illustrates the preparation of a granular herbicidal composition in accordance with the present invention and the phytotoxicity testing results achieved by applying these compositions to a variety of turfgrasses.

A granular composition of the present invention comprising 0.61 weight percent of Callisto® (a 40% mesotrione containing liquid formulation sold by Syngenta Crop Protection, Inc.) was combined with 99.39 weight percent of a granulated fertilizer by measuring and metering the liquid mesotrione into a rotating drum containing the granular fertilizer and mixing the ingredients thoroughly in the drum until the mesotrione was uniformly coated on and absorbed in the fertilizer granules.

The granular fertilizer employed to produce the composition for use in this example comprised a 25-3-10 formulation including urea, urea formaldehyde concentrate (UFC), potassium sulfate, monoammonium phosphate (MAP), ammonium sulfate with iron, manganese, zinc, copper, molybdenum and boron micronutrients. The fertilizer analysis comprised total nitrogen (TN) content of 25.61 weight percent based on the total fertilizer formulation, ammoniacal nitrogen content of 4.20 weight percent based on the total fertilizer formulation, urea nitrogen content of 11.47 weight percent based on the total fertilizer formulation, water soluble organic nitrogen content of 9.11 weight percent based on the total fertilizer formulation, and water insoluble nitrogen content from methylene ureas of 0.83 weight percent based on the total fertilizer formulation. The fertilizer analysis further comprised 3.14 weight percent based on the total fertilizer formulation of available phosphorus ($P_2O_5$); 10.24 weight percent based on the total fertilizer formulation of potash and 7.91 weight percent based on the total fertilizer formulation of sulfur.

The resulting composition produced by applying mesotrione on the fertilizer yielded a mesotrione analysis of 0.24% and this composition was evaluated for turfgrass injury by application on perennial ryegrass, fine fescue and tall fescue, at a rate of 0.33 lb mesotrione/acre (equivalent to an application rate of 137.5 lbs of the total composition/acre). In this regard, samples of the composition were pre-weighed and then each of the samples was applied, at the proper rate, in three replicated treatments to separate turf plots measuring 9 square feet each. Three comparable sized untreated check plots were employed as control plots to provide a reference point to demonstrate that untreated plots would not display any harm to the turfgrass.

Each treated test plot was irrigated after the composition was applied thereto and readings for turf injury were taken 14 days and 26 days after treatment ("DAT") for each of the test plots. A rating score scale of 0-10 was used for evaluation purposes where "0" indicated no injury and "10" indicated dead turf. Injury ratings above "1.5" were easily visible. The results of this testing representing an average of the three replications per treatment are tabulated in Table 1 as follows:

TABLE 1

Results Employing a Granular Fertilizer Mesotrione Composition

| | Turfgrass Injury (0-10 Rating Scale) | | | | | |
|---|---|---|---|---|---|---|
| | Perennial Ryegrass | | Fine Fescue | | Tall Fescue | |
| Treatment | 14 DAT | 26 DAT | 14 DAT | 26 DAT | 14 DAT | 26 DAT |
| Mesotrione/ Fertilizer Composition | 0.3 | 0 | 0 | 0 | 0.3 | 0 |
| Untreated Check Plot (Control) | 0 | 0 | 0 | 0 | 0 | 0 |

EXAMPLE 2

The mesotrione/fertilizer composition of Example 1 was evaluated for its efficacy in controlling dandelion (*Taraxacum officinale*), white clover (*Trifolium repens*), and crabgrass (*Digitaria sanguinalis*) weeds at the same application rate of 0.33 lb. mesotrione/acre as employed in Example 1. Samples of the composition of Example 1 were pre-weighed and then each of the samples was applied, at the proper rate, in three replicated treatments to separate test plots, measuring 9 square feet each, which were infested with these specific weeds. The results of this treatment were compared to three comparably sized untreated check plots (controls) to provide a reference demonstrating that untreated plots would display no weed control in the turfgrass.

Readings for initial weed control were taken 14 days after treatment ("DAT") and final readings for weed control were taken 28 days after treatment ("DAT") for each of the test plots. A rating score scale of 0-10 was used for initial weed control results after 14 days where "0" indicated no injury and "10" indicated dead weeds. A rating scale of 0-100 was used for weed control evaluation results after 28 days where "0" is no control and "100" is total weed control. The results of this testing representing an average of the three replications per treatment are tabulated in Table 2 as follows:

TABLE 2

Weed Control Results Employing a Granular Fertilizer Mesotrione Composition

| | Weed Control | | | | | |
|---|---|---|---|---|---|---|
| | Dandelion | | White Clover | | Crabgrass | |
| Treatment | 14 DAT Weed Control - (0-10 Rating Scale) | 28 DAT Weed Control - (0-100 Rating Scale) | 14 DAT Weed Control - (0-10 Rating Scale) | 28 DAT Weed Control - (0-100 Rating Scale) | 14 DAT Weed Control - (0-10 Rating Scale) | 28 DAT Weed Control - (0-100 Rating Scale) |
| Mesotrione/ Fertilizer Composition | 8.3 | 94.7 | 7.7 | 95 | 7.3 | 88.3 |
| Untreated Check Plot (Control) | 0 | 0 | 0 | 0 | 0 | 0 |

From the results of the testing as tabulated in Tables 1 and 2, it should be noted that the use of the compositions of the present invention on turfgrasses is safe to the particular species of turfgrasses tested and the compositions have been demonstrated to be effective in causing initial injury and longer term control of significant weeds in turf.

EXAMPLE 3

This example illustrates the phytotoxicity testing results achieved by applying liquid mesotrione alone to the same turfgrass varieties as tested in Example 1. As will be noted this test demonstrates the moderate to severe injury resulting from the spray application of liquid mesotrione to these turfgrasses as compared with the results ranging from no injury to only limited injury which were achieved when the compositions of the present invention comprising a granular fertilizer admixed with liquid mesotrione were employed to treat such grasses as exemplified by the results tabulated in Table 1.

In this example, mesotrione, in the form of Callisto® (40% mesotrione liquid), was evaluated as applied to the same turfgrasses of Example 1 (perennial ryegrass, fine fescue and tall fescue) for turfgrass injury at a rate of 0.33 lb mesotrione/acre. The mesotrione product was measured, placed in a sprayer with water and spray applied in three replicated treatments to separate test plots measuring 4 square feet each. The amount of water used was 2.6 gallons/1,000 square feet equivalent.

Readings for turf injury were taken 7 days, 20 days and 34 days after treatment ("DAT"). A rating scale of 0-100 was used for evaluation purposes where "0" indicated no injury and "100" indicated dead turf with ratings of 10 and above being undesirable. The results of this testing representing an average of the three replications per treatment are tabulated in Table 3 as follows:

TABLE 3

Results Employing a Liquid Mesotrione Spray Composition

| | Turfgrass Injury (0-100 Rating Scale) | | | | | | | | |
|---|---|---|---|---|---|---|---|---|---|
| | Perennial Ryegrass | | | Fine Fescue | | | Tall Fescue | | |
| Treatment | 7 DAT | 20 DAT | 34 DAT | 7 DAT | 20 DAT | 34 DAT | 7 DAT | 20 DAT | 34 DAT |
| Mesotrione Spray | 20 | 10 | 10 | 23.3 | 26.7 | 16.7 | 6.7 | 26.7 | 10 |
| Untreated Check Plot (Control) | 0 | 0 | 0 | 0 | 0 | 0 | 0 | 0 | 0 |

EXAMPLE 4

Spray applied liquid mesotrione as employed in Example 3 was evaluated for control of dandelion, clover, and crabgrass weeds at a rate of 0.33 lb mesotrione/acre. The liquid mesotrione test sample was measured, placed in a sprayer with water and spray applied in three replicated treatments to separate test plots measuring 4 square feet each at a rate of 0.33 lb mesotrione/acre. The amount of water used was 2.6 gallons/1,000 square feet equivalent.

Readings for weed control were taken 7 days, 26 days and/or 34 days after treatment ("DAT"). A rating scale of 0-100 was used for weed control evaluation where "0" is no control and "100" is total weed control. The results of this testing representing an average of the three replications per treatment are tabulated in Table 4 as follows:

TABLE 4

Weed Control Results Employing a Liquid Mesotrione Spray Composition

| | Weed Control (0-100 Rating Scale) | | | | | | | |
|---|---|---|---|---|---|---|---|---|
| | Dandelion | | | White Clover | | | Crabgrass | |
| Treatment | 7 DAT | 26 DAT | 34 DAT | 7 DAT | 26 DAT | 34 DAT | 7 DAT | 34 DAT |
| Mesotrione Spray | 46.7 | 99 | 93 | 40 | 50 | 76.7 | 70 | 31.7 |
| Untreated Check Plot (Control) | 0 | 0 | 0 | 0 | 0 | 0 | 0 | 0 |

From the results of the testing as tabulated in Tables 3 and 4, it should be noted that the use of the mesotrione spray treatments resulted in control of significant weeds in turf as expected. However, at the same application rate, the mesotrione sprays caused serious injury to the treated turfgrass species that would render this spray treatment commercially and functionally unacceptable.

EXAMPLE 5

This example further illustrates the preparation of a granular herbicidal composition in accordance with the present invention and the phytotoxicity testing results achieved by applying these compositions to perennial ryegrass and zoysiagrass.

A granular composition of the present invention comprising 0.205 weight percent of Callisto® (a 40% mesotrione containing liquid formulation sold by Syngenta Crop Protection, Inc.) was mixed with a solvent (hexylene glycol) at 1.30 weight percent and combined with 98.495 weight percent of a granulated fertilizer by measuring and metering the liquid mesotrione into a rotating drum containing the granular fertilizer and mixing the ingredients thoroughly in the drum until the mesotrione was uniformly coated on and absorbed in the fertilizer granules.

The granular fertilizer employed to produce the composition for use in this example comprised an 18-23-4 formulation including urea, urea formaldehyde concentrate (UFC), potassium sulfate, monoammonium phosphate (MAP), and ammonium sulfate. The fertilizer analysis comprised total nitrogen (TN) content of 18.00 weight percent based on the total fertilizer formulation, ammoniacal nitrogen content of 4.20 weight percent based on the total fertilizer formulation, urea nitrogen content of 7.20 weight percent based on the total fertilizer formulation, water soluble organic nitrogen content of 5.60 weight percent based on the total fertilizer formulation, and water insoluble nitrogen content from methylene ureas of 0.60 weight percent based on the total fertilizer formulation. The fertilizer analysis further comprised 23.00 weight percent based on the total fertilizer formulation of available phosphorus ($P_2O_5$); and 4.00 weight percent based on the total fertilizer formulation of potash.

The resulting composition produced by applying mesotrione on the fertilizer yielded a mesotrione analysis of 0.0820% and this composition was evaluated for turfgrass injury by application on perennial ryegrass and zoysiagrass at a rate of 0.15 lb mesotrione/acre (equivalent to an application rate of 181.20 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass.

Each treated test plot was irrigated after the composition was applied thereto and readings for turf injury were taken 7, 14, and/or 21 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Table 5 as follows:

TABLE 5

Comparative Results Employing Granular Fertilizer Mesotrione Compositions versus Liquid Mesotrione Spray Compositions

| | Pounds mesotrione/ acre | Turfgrass Injury Rating Scale 0-10, Injury ≥1.5 unacceptable | | |
|---|---|---|---|---|
| | | Perennial Ryegrass | | Zoysiagrass |
| Treatment | | 7 DAT | 21 DAT | 14 DAT |
| Mesotrione/ Fertilizer Composition | 0.15 | 0.2 | 0.2 | 0.6 |
| Mesotrione Liquid Spray | 0.15 | 1.8 | 2.0 | 2.0 |
| Untreated Check Plot (Control) | — | 0 | 0 | 0 |

EXAMPLE 6

This example further illustrates the preparation of a granular herbicidal composition in accordance with the present invention and the phytotoxicity testing results achieved by applying this composition to perennial ryegrass.

A granular composition of the present invention comprising 0.478 weight percent of Callisto® (a 40% mesotrione containing liquid formulation sold by Syngenta Crop Protection, Inc.) was mixed with a solvent (hexylene glycol) at 0.800 weight percent and combined with 98.722 weight percent of a granulated fertilizer by measuring and metering the liquid mesotrione into a rotating drum containing the granular fertilizer and mixing the ingredients thoroughly in the drum until the mesotrione was uniformly coated on and absorbed in the fertilizer granules.

The granular fertilizer employed to produce the composition for use in this example comprised a 28-3-3 formulation including urea, urea formaldehyde concentrate (UFC), potassium sulfate, monoammonium phosphate (MAP), and ammonium sulfate. The fertilizer analysis comprised total nitrogen (TN) content of 28.00 weight percent based on the total fertilizer formulation, ammoniacal nitrogen content of 9.00 weight percent based on the total fertilizer formulation, urea nitrogen content of 10.40 weight percent based on the total fertilizer formulation, water soluble organic nitrogen content of 7.90 weight percent based on the total fertilizer formulation, and water insoluble nitrogen content from methylene ureas of 0.70 weight percent based on the total fertilizer formulation. The fertilizer analysis further comprised 3.00 weight percent based on the total fertilizer formulation of available phosphorus ($P_2O_5$); 3.00 weight percent based on the total fertilizer formulation of potash and 11.00 weight percent based on the total fertilizer formulation of sulfur.

The resulting composition produced by applying mesotrione on the fertilizer yielded a mesotrione analysis of 0.191% and this composition was evaluated for turfgrass injury by application on perennial ryegrass at a rate of 0.25 lb mesotrione/acre (equivalent to an application rate of 130.50 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass.

Each treated test plot was irrigated after the composition was applied thereto and readings for turf injury were taken 7, 14, and/or 21 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Table 6 as follows:

TABLE 6

Comparative Results Employing Granular Fertilizer Mesotrione Compositions versus Liquid Mesotrione Spray Compositions

| Treatment | Pounds mesotrione/ acre | Turfgrass Injury Rating Scale 0-10, Injury ≥1.5 unacceptable Perennial Ryegrass | | |
|---|---|---|---|---|
| | | 7 DAT | 14 DAT | 21 DAT |
| Mesotrione/ Fertilizer Composition | 0.25 | 0.8 | 0.8 | 0.4 |
| Mesotrione Liquid Spray | 0.25 | 1.6 | 3.1 | 1.5 |

TABLE 6-continued

Comparative Results Employing Granular Fertilizer Mesotrione Compositions versus Liquid Mesotrione Spray Compositions

| Treatment | Pounds mesotrione/ acre | Turfgrass Injury Rating Scale 0-10, Injury ≥1.5 unacceptable Perennial Ryegrass | | |
|---|---|---|---|---|
| | | 7 DAT | 14 DAT | 21 DAT |
| Untreated Check Plot (Control) | — | 0 | 0 | 0 |

EXAMPLE 7

This example further illustrates the preparation of a granular herbicidal composition in accordance with the present invention and the phytotoxicity testing results achieved by applying this composition to perennial ryegrass and fine fescue turfgrasses.

A granular composition of the present invention comprising 0.631 weight percent of Callisto® (a 40% mesotrione containing liquid formulation sold by Syngenta Crop Protection, Inc.) was mixed with a solvent (hexylene glycol) at 0.700 weight percent and combined with 98.669 weight percent of a granulated fertilizer by measuring and metering the liquid mesotrione into a rotating drum containing the granular fertilizer and mixing the ingredients thoroughly in the drum until the mesotrione was uniformly coated on and absorbed in the fertilizer granules.

The granular fertilizer employed to produce the composition for use in this example comprised a 28-3-3 formulation including urea, urea formaldehyde concentrate (UFC), potassium sulfate, monoammonium phosphate (MAP), and ammonium sulfate. The fertilizer analysis comprised total nitrogen (TN) content of 28.00 weight percent based on the total fertilizer formulation, ammoniacal nitrogen content of 9.00 weight percent based on the total fertilizer formulation, urea nitrogen content of 10.40 weight percent based on the total fertilizer formulation, water soluble organic nitrogen content of 7.90 weight percent based on the total fertilizer formulation, and water insoluble nitrogen content from methylene ureas of 0.70 weight percent based on the total fertilizer formulation. The fertilizer analysis further comprised 3.00 weight percent based on the total fertilizer formulation of available phosphorus ($P_2O_5$); 3.0 weight percent based on the total fertilizer formulation of potash and 11.00 weight percent based on the total fertilizer formulation of sulfur.

The resulting composition produced by applying mesotrione on the fertilizer yielded a mesotrione analysis of 0.253% and this composition was evaluated for turfgrass injury by application on perennial ryegrass and fine fescue turfgrasses at a rate of 0.33 lb mesotrione/acre (equivalent to an application rate of 130.50 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots demonstrating that untreated plots would not display any harm to the turfgrass. The fine fescue testing results tabulated in Table 7 include results from two independent tests designated (1) and (2) in the table. Each test was conducted using the method previously described.

Each treated test plot was irrigated after the composition was applied thereto and readings for turf injury were taken 7, 14 and/or 21 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Table 7 as follows:

TABLE 7

Comparative Results Employing Granular Fertilizer Mesotrione Compositions versus Liquid Mesotrione Spray Compositions

| Treatment | Pounds mesotrione/ acre | Turfgrass Injury Rating Scale 0-10, Injury ≥1.5 unacceptable | | | |
|---|---|---|---|---|---|
| | | Perennial Ryegrass | Fine Fescue (1) | | Fine Fescue (2) |
| | | 14 DAT | 7 DAT | 21 DAT | 21 DAT |
| Mesotrione/ Fertilizer Composition | 0.33 | 0.3 | 0.3 | 1.0 | 0.8 |
| Mesotrione Liquid Spray | 0.33 | 2.1 | 1.8 | 1.8 | 2.2 |
| Untreated Check Plot (Control) | — | 0 | 0 | 0 | 0 |

EXAMPLE 8

This example further illustrates the preparation of a granular herbicidal composition in accordance with the present invention and the phytotoxicity testing results achieved by applying this composition to perennial ryegrass, tall fescue, and fine fescue turfgrasses.

A granular composition of the present invention comprising 0.957 weight percent of Callisto® (a 40% mesotrione containing liquid formulation sold by Syngenta Crop Protection, Inc.) was mixed with a solvent (hexylene glycol) at 0.400 weight percent and combined with 98.643 weight percent of a granulated fertilizer by measuring and metering the liquid mesotrione into a rotating drum containing the granular fertilizer and mixing the ingredients thoroughly in the drum until the mesotrione was uniformly coated on and absorbed in the fertilizer granules.

The granular fertilizer employed to produce the composition for use in this example comprised a 28-3-3 formulation including urea, urea formaldehyde concentrate (UFC), potassium sulfate, monoammonium phosphate (MAP), and ammonium sulfate. The fertilizer analysis comprised total nitrogen (TN) content of 28.00 weight percent based on the total fertilizer formulation, ammoniacal nitrogen content of 9.00 weight percent based on the total fertilizer formulation, urea nitrogen content of 10.40 weight percent based on the total fertilizer formulation, water soluble organic nitrogen content of 7.90 weight percent based on the total fertilizer formulation, and water insoluble nitrogen content from methylene ureas of 0.70 weight percent based on the total fertilizer formulation. The fertilizer analysis further comprised 3.00 weight percent based on the total fertilizer formulation of available phosphorus ($P_2O_5$); 3.0 weight percent based on the total fertilizer formulation of potash and 11.00 weight percent based on the total fertilizer formulation of sulfur.

The resulting composition produced by applying mesotrione on the fertilizer yielded a mesotrione analysis of 0.383% and this composition was evaluated for turfgrass injury by application on perennial ryegrass, tall fescue, and fine fescue turfgrasses at a rate of 0.50 lb mesotrione/acre (equivalent to an application rate of 130.50 lbs of the total composition/ acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass. The perennial ryegrass testing results tabulated in Table 8 include results from two independent tests designated (1) and (2) in the table. Each test was conducted using the method previously described.

Each treated test plot was irrigated after the composition was applied thereto and readings for turf injury were taken 7, 14, 21, and/or 28 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Tables 8 and 9 as follows:

TABLE 8

Comparative Results Employing Granular Fertilizer Mesotrione Compositions versus Liquid Mesotrione Spray Compositions

| Treatment | Pounds mesotrione/ acre | Turfgrass Injury Rating Scale 0-10, Injury ≥1.5 unacceptable | | | | | |
|---|---|---|---|---|---|---|---|
| | | Perennial Ryegrass (1) | | | Perennial Ryegrass (2) | | |
| | | 14 DAT | 21 DAT | 28 DAT | 7 DAT | 14 DAT | 21 DAT |
| Mesotrione/Fertilizer Composition | 0.5 | 0.7 | 0.3 | 0.2 | 0.8 | 0.5 | 0.5 |
| Mesotrione Liquid Spray | 0.5 | 3.8 | 2.2 | 2.0 | 4.1 | 6.2 | 3.6 |
| Untreated Check Plot (Control) | — | 0 | 0 | 0 | 0 | 0 | 0 |

TABLE 9

Comparative Results Employing Granular Fertilizer Mesotrione Compositions versus Liquid Mesotrione Spray Compositions

| Treatment | Pounds mesotrione/ acre | Turfgrass Injury Rating Scale 0-10, Injury ≥1.5 unacceptable | | | | | |
|---|---|---|---|---|---|---|---|
| | | Tall Fescue | | | Fine Fescue | | |
| | | 14 DAT | 21 DAT | 28 DAT | 7 DAT | 21 DAT | 28 DAT |
| Mesotrione/Fertilizer Composition | 0.5 | 0.4 | 0.2 | 0.4 | 0.5 | 1.2 | 0.3 |
| Mesotrione Liquid Spray | 0.5 | 2.8 | 3.0 | 2.1 | 1.8 | 3.6 | 2.6 |
| Untreated Check Plot (Control) | — | 0 | 0 | 0 | 0 | 0 | 0 |

EXAMPLE 9

This example further illustrates the preparation of a granular herbicidal composition in accordance with the present invention and the phytotoxicity testing results achieved by applying this composition to perennial ryegrass, tall fescue, centipedegrass, Kentucky bluegrass, and fine fescue.

A granular composition of the present invention comprising 1.913 weight percent of Callisto® (a 40% mesotrione containing liquid formulation sold by Syngenta Crop Protection, Inc.) was mixed with a solvent (hexylene glycol) at 0.200 weight percent and combined with 97.887 weight percent of a granulated fertilizer by measuring and metering the liquid mesotrione into a rotating drum containing the granular fertilizer and mixing the ingredients thoroughly in the drum until the mesotrione was uniformly coated on and absorbed in the fertilizer granules.

The granular fertilizer employed to produce the composition for use in this example comprised a 28-3-3 formulation including urea, urea formaldehyde concentrate (UFC), potassium sulfate, monoammonium phosphate (MAP), and ammonium sulfate. The fertilizer analysis comprised total nitrogen (TN) content of 28.00 weight percent based on the total fertilizer formulation, ammoniacal nitrogen content of 9.00 weight percent based on the total fertilizer formulation, urea nitrogen content of 10.40 weight percent based on the total fertilizer formulation, water soluble organic nitrogen content of 7.90 weight percent based on the total fertilizer formulation, and water insoluble nitrogen content from methylene ureas of 0.70 weight percent based on the total fertilizer formulation. The fertilizer analysis further comprised 3.00 weight percent based on the total fertilizer formulation of available phosphorus ($P_2O_5$); 3.00 weight percent based on the total fertilizer formulation of potash and 11.00 weight percent based on the total fertilizer formulation of sulfur.

The resulting composition produced by applying mesotrione on the fertilizer yielded a mesotrione analysis of 0.765% and this composition was evaluated for turfgrass injury by application on perennial ryegrass, tall fescue, centipedegrass, Kentucky bluegrass, and fine fescue at a rate of 1.00 lb mesotrione/acre (equivalent to an application rate of 130.50 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass. The perennial ryegrass test results tabulated in Table 10 include results from three independent tests designated (1), (2) and (3) in the table. Each test was conducted using the method previously described. The tall fescue test results tabulated in Table 11 include results from two independent tests designated (1) and (2) in the table. Each test was conducted using the method previously described. The Kentucky bluegrass test results tabulated in Table 12 include results from two independent tests designated (1) and (2) in the table. Each test was conducted using the method previously described.

Each treated test plot was irrigated after the composition was applied thereto and readings for turf injury were taken 7, 14, 21, and/or 28 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Tables 10, 11, and 12 as follows:

TABLE 10

Comparative Results Employing Granular Fertilizer Mesotrione Compositions versus Liquid Mesotrione Spray Compositions

| | | Turfgrass Injury Rating Scale 0-10, Injury ≥1.5 unacceptable | | | | |
|---|---|---|---|---|---|---|
| | Pounds mesotrione/ | Perennial Ryegrass (1) | Perennial Ryegrass (2) | | Perennial Ryegrass (3) | |
| Treatment | acre | 28 DAT | 21 DAT | 28 DAT | 7 DAT | 21 DAT |
| Mesotrione/Fertilizer Composition | 1.0 | 0 | 0.9 | 0.5 | 0.9 | 1.2 |
| Mesotrione Liquid Spray | 1.0 | 3.8 | 6.6 | 2.1 | 5.2 | 7.2 |
| Untreated Check Plot (Control) | — | 0 | 0 | 0 | 0 | 0 |

TABLE 11

Comparative Results Employing Granular Fertilizer Mesotrione Compositions versus Liquid Mesotrione Spray Compositions

| | | Turfgrass Injury Rating Scale 0-10, Injury ≥1.5 unacceptable | | | | |
|---|---|---|---|---|---|---|
| | Pounds mesotrione/ | Tall Fescue (1) | Tall Fescue (2) | | Fine Fescue | Centipede-grass |
| Treatment | acre | 28 DAT | 21 DAT | 28 DAT | 7 DAT | 14 DAT |
| Mesotrione/Fertilizer Composition | 1.0 | 1.0 | 0.9 | 1.0 | 0.9 | 0.4 |
| Mesotrione Liquid Spray | 1.0 | 1.5 | 5.8 | 4.0 | 3.0 | 1.5 |
| Untreated Check Plot (Control) | — | 0 | 0 | 0 | 0 | 0 |

TABLE 12

Comparative Results Employing Granular Fertilizer Mesotrione Compositions versus Liquid Mesotrione Spray Compositions

| | | Turfgrass Injury Rating Scale 0-10, Injury ≥1.5 unacceptable | | | | |
|---|---|---|---|---|---|---|
| | Pounds mesotrione/ | Kentucky Bluegrass (1) | | | Kentucky Bluegrass (2) | |
| Treatment | acre | 14 DAT | 21 DAT | 28 DAT | 14 DAT | 21 DAT |
| Mesotrione/Fertilizer Composition | 1.0 | 1.4 | 0.2 | 0.1 | 0.8 | 0.5 |
| Mesotrione Liquid Spray | 1.0 | 4.6 | 2.9 | 1.6 | 2.2 | 1.5 |
| Untreated Check Plot (Control) | — | 0 | 0 | 0 | 0 | 0 |

EXAMPLE 10

This example further illustrates the preparation of a granular herbicidal composition in accordance with the present invention and the phytotoxicity testing results achieved by applying this composition to perennial ryegrass and zoysiagrass.

A granular composition of the present invention comprising 0.631 weight percent of Callisto® (a 40% mesotrione containing liquid formulation sold by Syngenta Crop Protection, Inc.) was mixed with a solvent (hexylene glycol) at 0.700 weight percent and combined with 99.669 weight percent of a pelletized gypsum granule by measuring and metering the liquid mesotrione into a rotating drum containing the pelletized gypsum and mixing the ingredients thoroughly in the drum until the mesotrione was uniformly coated on and absorbed in the pelletized gypsum granules. The pelletized gypsum employed to produce the composition for use in this example contained 21.0% calcium and 16.0% sulfur.

The resulting composition produced by applying mesotrione on the pelletized gypsum granule yielded a mesotrione analysis of 0.252% and this composition was evaluated for turfgrass injury by application on perennial ryegrass and zoysiagrass at a rate of 0.15 lb mesotrione/acre (equivalent to an application rate of 59.50 lbs of the total composition/ acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass.

Each treated test plot was irrigated after the composition was applied thereto and readings for turf injury were taken 7, 14, and/or 21 days after treatment ("DAT") for each of the test plots. A rating score scale of 0-10 was used for evaluation purposes where "0" indicated no injury and "10" indicated dead turf Turfgrass injury at a level of "1.5" and greater was easily visible and considered unacceptable. The results of this testing representing an average of the four replications per treatment are tabulated in Table 13 as follows:

TABLE 13

Comparative Results Employing Inert Granular Mesotrione Compositions versus Liquid Mesotrione Spray Compositions

| Treatment | Pounds mesotrione/ acre | Turfgrass Injury Rating Scale 0-10, Injury ≥1.5 unacceptable | | |
|---|---|---|---|---|
| | | Perennial Ryegrass | | Zoysiagrass |
| | | 7 DAT | 21 DAT | 14 DAT |
| Mesotrione/ Inert Granular Composition | 0.15 | 0.3 | 0.4 | 0.2 |
| Mesotrione Liquid Spray | 0.15 | 1.8 | 2.0 | 2.0 |
| Untreated Check Plot (Control) | — | 0 | 0 | 0 | percent of a pelletized gypsum granule by measuring and metering the liquid mesotrione into a rotating drum containing the pelletized gypsum and mixing the ingredients thoroughly in the drum until the mesotrione was uniformly coated on and absorbed in the pelletized gypsum granules. The pelletized gypsum employed to produce the composition for use in this example contained 21.0% calcium and 16.0% sulfur.

The resulting composition produced by applying mesotrione on the pelletized gypsum granule yielded a mesotrione analysis of 0.252% and this composition was evaluated for turfgrass injury by application on perennial ryegrass, fine fescue, and zoysiagrass at a rate of 0.25 lb mesotrione/acre (equivalent to an application rate of 99.20 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass.

Each treated test plot was irrigated after the composition was applied thereto and readings for turf injury were taken 7, 14, and/or 21 days after treatment ("DAT") for each of the test plots. A rating score scale of 0-10 was used for evaluation purposes where "0" indicated no injury and "10" indicated dead turf Turfgrass injury at a level of "1.5" and greater was easily visible and considered unacceptable. The results of this testing representing an average of the four replications per treatment are tabulated in Table 14 as follows:

TABLE 14

Comparative Results Employing Inert Granular Mesotrione Compositions versus Liquid Mesotrione Spray Compositions

| Treatment | Pounds mesotrione/ acre | Turfgrass Injury Rating Scale 0-10, Injury ≥1.5 unacceptable | | | | | |
|---|---|---|---|---|---|---|---|
| | | Perennial Ryegrass | | | Fine Fescue | Zoysiagrass | |
| | | 7 DAT | 14 DAT | 21 DAT | 7 DAT | 14 DAT | 21 DAT |
| Mesotrione/Inert Granular Composition | 0.25 | 0.2 | 0.3 | 0.3 | 0.2 | 0.6 | 0.5 |
| Mesotrione Liquid Spray | 0.25 | 1.6 | 3.1 | 1.5 | 1.6 | 5.6 | 2.8 |
| Untreated Check Plot (Control) | — | 0 | 0 | 0 | 0 | 0 | 0 |

EXAMPLE 11

This example further illustrates the preparation of a granular herbicidal composition in accordance with the present invention and the phytotoxicity testing results achieved by applying this composition to perennial ryegrass, fine fescue, and zoysiagrass.

A granular composition of the present invention comprising 0.631 weight percent of Callisto® (a 40% mesotrione containing liquid formulation sold by Syngenta Crop Protection, Inc.) was mixed with a solvent (hexylene glycol) at 0.700 weight percent and combined with 99.669 weight

EXAMPLE 12

This example further illustrates the preparation of a granular herbicidal composition in accordance with the present invention and the phytotoxicity testing results achieved by applying this composition to perennial ryegrass, fine fescue, tall fescue and zoysiagrass.

A granular composition of the present invention comprising 0.631 weight percent of Callisto® (a 40% mesotrione containing liquid formulation sold by Syngenta Crop Protection, Inc.) was mixed with a solvent (hexylene glycol) at 0.700 weight percent and combined with 99.669 weight percent of a pelletized gypsum granule by measuring and metering the liquid mesotrione into a rotating drum containing the pelletized gypsum and mixing the ingredients thoroughly in the drum until the mesotrione was uniformly coated on and absorbed in the pelletized gypsum granules. The pelletized gypsum employed to produce the composition for use in this example contained 21.0% calcium and 16.0% sulfur.

The resulting composition produced by applying mesotrione on the pelletized gypsum granule yielded a mesotrione analysis of 0.252% and this composition was evaluated for turfgrass injury by application on perennial ryegrass, fine fescue, tall fescue and zoysiagrass at a rate of 0.33 lb mesotrione/acre (equivalent to an application rate of 130.90 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass. The perennial ryegrass testing results tabulated in Table 15 include results from two independent tests designated (1) and (2) in the table. Each test was conducted using the method previously described. The fine fescue test results tabulated in Table 16 include results from two independent tests designated (1) and (2) in the table. Each test was conducted using the method previously described.

Each treated test plot was irrigated after the composition was applied thereto and readings for turf injury were taken 7, 14 and/or 21 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Tables 15 and 16 as follows:

TABLE 15

Comparative Results Employing Inert Granular Mesotrione Compositions versus Liquid Mesotrione Spray Compositions

| | | Turfgrass Injury Rating Scale 0-10, Injury ≥1.5 unacceptable | | | | |
| --- | --- | --- | --- | --- | --- | --- |
| Treatment | Pounds mesotrione/ acre | Perennial Ryegrass (1) 14 DAT | Perennial Ryegrass (2) 14 DAT | 21 DAT | Tall Fescue 14 DAT | 21 DAT |
| Mesotrione/Inert Granular Composition | 0.33 | 0.3 | 0.9 | 0.8 | 0.3 | 0.4 |
| Mesotrione Liquid Spray | 0.33 | 2.1 | 4.4 | 2.9 | 2.2 | 3.4 |
| Untreated Check Plot (Control) | — | 0 | 0 | 0 | 0 | 0 |

TABLE 16

Comparative Results Employing Inert Granular Mesotrione Compositions versus Liquid Mesotrione Spray Compositions

| | | Turfgrass Injury Rating Scale 0-10, Injury ≥1.5 unacceptable | | | | | |
| --- | --- | --- | --- | --- | --- | --- | --- |
| Treatment | Pounds mesotrione/ acre | Fine Fescue (1) 7 DAT | 14 DAT | 21 DAT | Fine Fescue (2) 21 DAT | Zoysiagrass 14 DAT | 21 DAT |
| Mesotrione/Inert Granular Composition | 0.33 | 0.2 | 1.3 | 1.0 | 0.6 | 0.6 | 1.1 |
| Mesotrione Liquid Spray | 0.33 | 1.8 | 3.9 | 1.8 | 2.2 | 4.7 | 3.4 |
| Untreated Check Plot (Control) | — | 0 | 0 | 0 | 0 | 0 | 0 |

EXAMPLE 13

This example further illustrates the preparation of a granular herbicidal composition in accordance with the present invention and the phytotoxicity testing results achieved by applying this composition to fine fescue, tall fescue, perennial ryegrass, St. Augustinegrass and zoysiagrass.

A granular composition of the present invention comprising 0.631 weight percent of Callisto® (a 40% mesotrione containing liquid formulation sold by Syngenta Crop Protection, Inc.) was mixed with a solvent (hexylene glycol) at 0.700 weight percent and combined with 99.669 weight percent of a pelletized gypsum granule by measuring and metering the liquid mesotrione into a rotating drum containing the pelletized gypsum and mixing the ingredients thoroughly in the drum until the mesotrione was uniformly coated on and absorbed in the pelletized gypsum granules. The pelletized gypsum employed to produce the composition for use in this example contained 21.0% calcium and 16.0% sulfur.

The resulting composition produced by applying mesotrione on the pelletized gypsum granule yielded a mesotrione analysis of 0.252% and this composition was evaluated for turfgrass injury by application on fine fescue, tall fescue, perennial ryegrass, St. Augustinegrass and zoysiagrass at a rate of 0.50 lb mesotrione/acre (equivalent to an application rate of 198.40 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass. The perennial ryegrass test results tabulated in Table 17 include results from two independent tests designated (1) and (2) in the table. Each test was conducted using the method previously described. The fine fescue test results tabulated in Table 17 include results from two independent tests designated (1) and (2) in the table. Each test was conducted using the method previously described. The tall fescue test results tabulated in Table 18 include results from two independent tests designated (1) and (2) in the table. Each test was conducted using the method previously described.

Each treated test plot was irrigated after the composition was applied thereto and readings for turf injury were taken 7, 14, 21, and/or 28 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Tables 17 and 18 as follows:

TABLE 17

Comparative Results Employing Inert Granular Mesotrione Compositions versus Liquid Mesotrione Spray Compositions

| | | Turfgrass Injury Rating Scale 0-10, Injury ≥1.5 unacceptable | | | | | |
|---|---|---|---|---|---|---|---|
| Treatment | Pounds mesotrione/ acre | Perennial Ryegrass (1) | | Perennial Ryegrass (2) | | Fine Fescue (1) | Fine Fescue (2) |
| | | 21 DAT | 28 DAT | 7 DAT | 14 DAT | 21 DAT | 7 DAT | 7 DAT |
| Mesotrione/ Inert Granule Composition | 0.5 | 0.6 | 1.0 | 1.3 | 1.4 | 1.4 | 0.6 | 0.5 |
| Mesotrione Liquid Spray | 0.5 | 2.2 | 2.0 | 4.1 | 6.2 | 3.6 | 1.5 | 1.8 |
| Untreated Check Plot (Control) | — | 0 | 0 | 0 | 0 | 0 | 0 | 0 |

TABLE 18

Comparative Results Employing Inert Granular Mesotrione Compositions versus Liquid Mesotrione Spray Compositions

| | | Turfgrass Injury Rating Scale 0-10, Injury ≥1.5 unacceptable | | | | | |
|---|---|---|---|---|---|---|---|
| Treatment | Pounds mesotrione/ acre | Tall Fescue (1) | | | Tall Fescue (2) | | St. Augustine-Grass | Zoysia-grass |
| | | 14 DAT | 21 DAT | 28 DAT | 14 DAT | 21 DAT | 7 DAT | 14 DAT |
| Mesotrione/ Inert Granular Compositions | 0.5 | 0.4 | 0.4 | 0.9 | 1.0 | 0.9 | 0.4 | 1.3 |
| Mesotrione Liquid Spray | 0.5 | 2.8 | 3.0 | 2.1 | 3.4 | 3.1 | 1.8 | 6.4 |
| Untreated Check Plot (Control) | — | 0 | 0 | 0 | 0 | 0 | 0 | 0 |

EXAMPLE 14

This example further illustrates the preparation of a granular herbicidal composition in accordance with the present invention and the phytotoxicity testing results achieved by applying this composition to tall fescue, Kentucky bluegrass, fine fescue, and St. Augustinegrass.

A granular composition of the present invention comprising 0.631 weight percent of Callisto® (a 40% mesotrione containing liquid formulation sold by Syngenta Crop Protection, Inc.) was mixed with a solvent (hexylene glycol) at 0.700 weight percent and combined with 99.669 weight percent of a pelletized gypsum granule by measuring and metering the liquid mesotrione into a rotating drum containing the pelletized gypsum and mixing the ingredients thoroughly in the drum until the mesotrione was uniformly coated on and absorbed in the pelletized gypsum granules. The pelletized gypsum employed to produce the composition for use in this example contained 21.0% calcium and 16.0% sulfur.

The resulting composition produced by applying mesotrione on the pelletized gypsum granule yielded a mesotrione analysis of 0.252% and this composition was evaluated for turfgrass injury by application on tall fescue, Kentucky bluegrass, fine fescue, and St. Augustinegrass at a rate of 1.00 lb mesotrione/acre (equivalent to an application rate of 396.80 lbs of the total composition/acre). In this regard, samples of the composition were pre-weighed and then each of the samples was applied, at the proper rate, in four replicated treatments to separate turf plots measuring 9 square feet each. Four comparable sized untreated check plots were employed as control plots to provide a reference point to demonstrate that untreated plots would not display any harm to the turfgrass. The tall fescue testing results tabulated in Table 19 include results from three independent tests designated (1), (2) and (3) in the table. Each test was conducted using the method previously described. The Kentucky bluegrass test results tabulated in Table 20 include results from two independent tests designated (1) and (2) in the table. Each test was conducted using the method previously described.

Each treated test plot was irrigated after the composition was applied thereto and readings for turf injury were taken 7, 14, 21, and/or 28 days after treatment ("DAT") for each of the test plots. A rating score scale of 0-10 was used for evaluation purposes where "0" indicated no injury and "10" indicated dead turf. Turfgrass injury at a level of "1.5" and greater was easily visible and considered unacceptable. The results of this testing representing an average of the four replications per treatment are tabulated in Tables 19 and 20 as follows:

TABLE 19

Comparative Results Employing Inert Granular Mesotrione Compositions versus Liquid Mesotrione Spray Compositions

| | | Turfgrass Injury Rating Scale 0-10, Injury ≥1.5 unacceptable | | | | | |
|---|---|---|---|---|---|---|---|
| Treatment | Pounds mesotrione/ acre | Tall Fescue (1) 28 DAT | Tall Fescue (2) 14 DAT | 21 DAT | 28 DAT | Tall Fescue (3) 7 DAT | 21 DAT |
| Mesotrione/ Inert Granular Compositions | 1.0 | 0.6 | 1.4 | 0.9 | 1.2 | 0.2 | 1.4 |
| Mesotrione Liquid Spray | 1.0 | 1.5 | 7.0 | 5.8 | 4.0 | 1.6 | 6.8 |
| Untreated Check Plot (Control) | — | 0 | 0 | 0 | 0 | 0 | 0 |

TABLE 20

Comparative Results Employing Inert Granular Mesotrione Compositions versus Liquid Mesotrione Spray Compositions

| | | Turfgrass Injury Rating Scale 0-10, Injury ≥1.5 unacceptable | | | | | | |
|---|---|---|---|---|---|---|---|---|
| Treatment | Pounds mesotrione/ acre | Kentucky Bluegrass (1) 14 DAT | 21 DAT | 28 DAT | Kentucky Bluegrass (2) 14 DAT | 21 DAT | Fine Fescue 7 DAT | St. Augustine-grass 7 DAT |
| Mesotrione/ Inert Granule Composition | 1.0 | 1.3 | 0.5 | 0.5 | 0.8 | 0.2 | 0.8 | 0.9 |
| Mesotrione Liquid Spray | 1.0 | 4.6 | 2.9 | 1.6 | 2.2 | 1.5 | 3.0 | 4.9 |
| Untreated Check Plot (Control) | — | 0 | 0 | 0 | 0 | 0 | 0 | 0 |

EXAMPLE 15

The mesotrione/fertilizer and mesotrione/inert granule compositions of Examples 6, 7, 11, and 12 were evaluated for their efficacy in controlling dollarweed (Hydrocotyle umbellata) at the same application rate of 0.25 lb and 0.33 lb. mesotrione/acre. Samples of the composition of Examples 6, 7, 11, and 12 were pre-weighed and then each of the samples was applied, at the proper rate, in four replicated treatments to separate test plots measuring four square feet each, which were infested with these specific weeds. The results of these treatments were compared to mesotrione liquid spray treatments to show comparable weed control activity between liquid and granule mesotrione products. In addition, untreated check plots (controls) of the same size were included in the test to provide a reference demonstrating that untreated plots would display no weed control in the turfgrass.

In this example, liquid mesotrione, in the form of Callisto® (40% mesotrione liquid), was evaluated as applied to dollarweed at rates of 0.25 lb and 0.33 lb mesotrione/acre. The mesotrione product amount for each application rate was measured out and placed in a sprayer and spray applied in a single pass using an automated spray booth in four replicated treatments to separate test plants. The spray chamber interior area measuring 13.77 square feet received application of the spray with each of four replications. The amount of water used was 2.3 gallons/1,000 square feet equivalent.

Readings for initial weed control were taken 9 days after treatment ("DAT") and final readings for weed control were taken 28 days after treatment ("DAT") for each of the test plots. A rating scale of 0-100 was used for weed control evaluation results where "0" is no control and "100" is total weed control. The results of this testing representing an average of the four replications per treatment are tabulated in Table 21 as follows:

TABLE 21

Comparative Weed Control Results Employing Granular Fertilizer Mesotrione and Inert Granule Mesotrione Compositions versus Liquid Mesotrione Spray Compositions

| Treatments | Pounds mesotrione/acre | Weed Control Rating Scale 0-100 Dollarweed | |
|---|---|---|---|
| | | 9 DAT | 28 DAT |
| Mesotrione/Fertilizer Composition | 0.25 | 27.5 | 65.0 |
| Mesotrione/Fertilizer Composition | 0.33 | 30.0 | 65.0 |
| Mesotrione/Inert Granule Composition | 0.25 | 18.8 | 65.0 |
| Mesotrione/Inert Granule Composition | 0.33 | 29.0 | 65.0 |
| Mesotrione Liquid Spray | 0.25 | 12.5 | 60.0 |
| Mesotrione Liquid Spray | 0.33 | 15.0 | 67.5 |
| Untreated Check Plot (Control) | — | 0 | 0 |

From the results of the testing as tabulated in Tables 6, 7, 14-16 and 21 it should be noted that the use of the compositions of the present invention on turfgrasses are safe to the particular species of turfgrasses tested and the compositions have been demonstrated to be effective in providing control of weeds, such as dollarweed, in turf. The use of the mesotrione liquid spray treatments resulted in dollarweed control as expected. However, at the same application rates, the mesotrione sprays caused significant injury to previously referenced treated turfgrass species that would render this spray treatment on a broad scale basis commercially and functionally unacceptable.

EXAMPLE 16

The mesotrione/fertilizer and mesotrione/inert granule compositions of Examples 7, 8, 9, 12, 13, and 14 were evaluated for their efficacy in controlling white clover (Trifolium repens) at the same application rate of 0.33, 0.50, and 1.0 lb. mesotrione/acre. Samples of the composition of Examples 7, 8, 9, 12, 13, and 14 were pre-weighed and then each of the samples was applied, at the proper rate, in four replicated treatments to separate test plots measuring 9 square feet each, which were infested with white clover. The results of these treatments were compared to mesotrione liquid spray treatments to show comparable weed control activity between liquid and granule mesotrione products. In addition, untreated check plots (controls) of the same size were included in the test to provide a reference demonstrating that untreated plots would display no weed control in the turfgrass.

In this example, liquid mesotrione, in the form of Callisto® (40% mesotrione liquid), was evaluated as applied to turfgrass infested with white clover at rates of 0.33, 0.50 and 1.0 lb mesotrione/acre. The mesotrione product amount for each application rate was measured out and placed in a sprayer (U.S. Pat. Nos. 6,415,956 and 6,170,706) and spray applied in four replicated treatments to separate test plots measuring 9 square feet each. The amount of water used was 3.6 gallons/1,000 square feet equivalent.

Readings for weed control were taken 21 and 28 days after treatment ("DAT") for each of the test plots. A rating scale of 0-100 was used for weed control evaluation results where "0" is no control and "100" is total weed control. The results of this testing representing an average of the four replications per treatment are tabulated in Tables 22 and 23 as follows:

TABLE 22

Comparative Weed Control Results Employing Granular Fertilizer Mesotrione and Inert Granule Mesotrione Compositions versus Liquid Mesotrione Spray Compositions

| Treatments | Pounds mesotrione/acre | Weed Control Rating Scale 0-100 White Clover | |
|---|---|---|---|
| | | 21 DAT | 28 DAT |
| Mesotrione/Fertilizer Composition | 0.33 | 42.5 | 47.5 |
| Mesotrione/Fertilizer Composition | 0.5 | 52.5 | 67.5 |
| Mesotrione/Fertilizer Composition | 1.0 | 78.8 | 87.3 |
| Mesotrione/Inert Granule Composition | 0.33 | 45 | 50 |
| Mesotrione/Inert Granule Composition | 0.5 | 63.8 | 70.0 |
| Mesotrione/Inert Granule Composition | 1.0 | 82.5 | 91.3 |
| Mesotrione Liquid Spray | 0.33 | 55.0 | 50.0 |
| Mesotrione Liquid Spray | 0.5 | 83.8 | 88.8 |
| Mesotrione Liquid Spray | 1.0 | 92.5 | 97.0 |
| Untreated Check Plot (Control) | — | 0 | 0 |

TABLE 23

Comparative Weed Control Results Employing Granular
Fertilizer Mesotrione and Inert Granule Mesotrione Compositions
versus Liquid Mesotrione Spray Compositions

| Treatments | Pounds mesotrione/ acre | Weed Control Rating Scale 0-100 White Clover | |
|---|---|---|---|
| | | 21 DAT | 28 DAT |
| Mesotrione/Fertilizer Composition | 0.33 | 50.0 | 60.0 |
| Mesotrione/Fertilizer Composition | 0.5 | 50.0 | 50.0 |
| Mesotrione/Fertilizer Composition | 1.0 | 80.0 | 77.5 |
| Mesotrione/Inert Granule Composition | 0.33 | 42.5 | 42.5 |
| Mesotrione/Inert Granule Composition | 0.5 | 56.3 | 55.0 |
| Mesotrione/Inert Granule Composition | 1.0 | 87.5 | 66.3 |
| Mesotrione Liquid Spray | 0.33 | 47.5 | 40.0 |
| Mesotrione Liquid Spray | 0.5 | 75.0 | 63.8 |
| Mesotrione Liquid Spray | 1.0 | 94.5 | 80.0 |
| Untreated Check Plot (Control) | — | 0 | 0 |

From the results of the testing as tabulated in Tables 7-12 and 15-23, it should be noted that the use of the compositions of the present invention on turfgrasses are safe to the particular species of turfgrasses tested and the compositions have been demonstrated to be effective in providing control of weeds, such as white clover, in turf. The use of the mesotrione liquid spray treatments resulted in white clover control as expected. However, at the same application rates, the mesotrione sprays caused significant injury to previously referenced treated turfgrass species that would render this spray treatment on a broad scale basis commercially and functionally unacceptable.

Although the invention has been described in its preferred forms with a certain degree of particularity, it is to be understood that the present disclosure has been made by way of example only. Numerous changes in the details of the compositions and ingredients therein as well as the methods of preparation and use will be apparent to those skilled in the art without departing from the spirit and scope of the invention as defined in the appended claims.

The invention claimed is:

1. A granular composition comprising mesotrione coated on or impregnated into a granular substrate material, wherein the quantity of mesotrione in the composition ranges from about 0.05% to about 1% by weight of the composition.

2. The composition of claim 1, wherein the granular substrate material comprises a solid fertilizer granule.

3. The composition of claim 2, wherein the solid fertilizer granule comprises organic and inorganic nitrogen-containing compounds, potassium salts, phosphoric acid, salts of phosphoric acid, or mixtures thereof.

4. The composition of claim 2, wherein the solid fertilizer granule ranges from about 1.0 to about 5.0 mm in diameter.

5. The composition of claim 2, wherein said solid fertilizer granule comprises about 1 to about 40% by weight nitrogen, about 1 to about 30% by weight phosphorous, and about 1 to about 20% by weight potassium.

6. The composition of claim 2, wherein the quantity of mesotrione in the composition is about 0.05% to about 0.5% by weight of the composition.

7. The composition of claim 2, wherein the mesotrione is coated on said solid fertilizer granule and the quantity of mesotrione in the composition is 0.0820% by weight of the composition.

8. The composition of claim 1, wherein the granular substrate material is an inert solid carrier.

9. The composition of claim 8, wherein the inert solid carrier comprises corncobs, peanut hulls, processed paper pulp, sawdust, limestone, gypsum, sand, vermiculite, perlite, fuller's earth, attapulgite clays, bentonite clays, montmorillonite clays, or mixtures thereof.

10. The composition of claim 8, wherein the quantity of mesotrione in the composition is about 0.075% to about 0.4% by weight of the composition.

11. A method for controlling the growth of weeds in a turfgrass comprising applying a composition comprising mesotrione coated on or impregnated into a granular substrate material to the turfgrass, wherein the quantity of mesotrione in the composition ranges from about 0.05% to about 1% by weight of the composition.

12. The method of claim 11, wherein the granular substrate material is a solid fertilizer granule.

13. The method of claim 12, wherein the solid fertilizer granule comprises organic and inorganic nitrogen-containing compounds, potassium salts, phosphoric acid, salts of phosphoric acid, or mixtures thereof.

14. The method of claim 12, wherein the solid fertilizer granule ranges from about 1.0 to about 5.0 mm in diameter.

15. The method of claim 12, wherein said solid fertilizer granule comprises about 1 to about 40% by weight nitrogen, about 1 to about 30% by weight phosphorous, and about 1 to about 20% by weight potassium.

16. The method of claim 12, wherein the quantity of mesotrione in the composition is about 0.05% to about 0.5% by weight of the composition.

17. The method of claim 12, wherein the mesotrione is coated on said solid fertilizer granule and the quantity of mesotrione in the composition is 0.0820% by weight of the composition.

18. The method of claim 11, wherein the granular substrate material is an inert solid carrier.

19. The method of claim 18, wherein the quantity of mesotrione in the composition is about 0.075% to about 0.4% by weight of the composition.

20. The method of claim 11, wherein the turfgrass comprises fine fescue, tall fescue, perennial ryegrass, St. Augustinegrass, Kentucky Bluegrass, zoysiagrass, centipedegrass, or mixtures thereof.

* * * * *